US011944500B2

(12) United States Patent
Specht et al.

(10) Patent No.: US 11,944,500 B2
(45) Date of Patent: Apr. 2, 2024

(54) DETERMINING MATERIAL STIFFNESS USING MULTIPLE APERTURE ULTRASOUND

(71) Applicant: MAUI IMAGING, INC., San Jose, CA (US)

(72) Inventors: Donald F. Specht, Los Altos, CA (US); Kenneth D. Brewer, Santa Clara, CA (US)

(73) Assignee: Maui Imaging, Inc., San Jose, CA (US)

(*) Notice: Subject to any disclaimer, the term of this patent is extended or adjusted under 35 U.S.C. 154(b) by 851 days.

(21) Appl. No.: 16/897,116

(22) Filed: Jun. 9, 2020

(65) Prior Publication Data

US 2020/0297320 A1 Sep. 24, 2020

Related U.S. Application Data

(60) Continuation of application No. 15/155,908, filed on May 16, 2016, now Pat. No. 10,675,000, which is a
(Continued)

(51) Int. Cl.
*A61B 8/00* (2006.01)
*A61B 8/08* (2006.01)
(Continued)

(52) U.S. Cl.
CPC .............. *A61B 8/485* (2013.01); *A61B 8/145* (2013.01); *A61B 8/4444* (2013.01);
(Continued)

(58) Field of Classification Search
CPC ....... A61B 8/485; A61B 8/145; A61B 8/4444; A61B 8/4477; A61B 8/4488; A61B 8/461;
(Continued)

(56) References Cited

U.S. PATENT DOCUMENTS

| 5,871,446 A | 2/1999 | Wilk |
| 2007/0083109 A1 | 4/2007 | Ustuner et al. |

(Continued)

FOREIGN PATENT DOCUMENTS

KR 1020130060875 A 6/2013

OTHER PUBLICATIONS

Lockwood et al.; Real-time 3-D ultrasound imaging using sparse synthetic aperture beamforming; IEEE transactions on ultrasonics, ferroelectrics, and frequency control; 45(4); pp. 980-988, Jul. 1998.

*Primary Examiner* — Patricia J Park
(74) *Attorney, Agent, or Firm* — Shay Glenn LLP

(57) ABSTRACT

Changes in tissue stiffness have long been associated with disease. Systems and methods for determining the stiffness of tissues using ultrasonography may include a device for inducing a propagating shear wave in tissue and tracking the speed of propagation, which is directly related to tissue stiffness and density. The speed of a propagating shear wave may be detected by imaging a tissue at a high frame rate and detecting the propagating wave as a perturbance in successive image frames relative to a baseline image of the tissue in an undisturbed state. In some embodiments, sufficiently high frame rates may be achieved by using a ping-based ultrasound imaging technique in which unfocused omnidirectional pings are transmitted (in an imaging plane or in a hemisphere) into a region of interest. Receiving echoes of the omnidirectional pings with multiple receive apertures allows for substantially improved lateral resolution.

10 Claims, 8 Drawing Sheets

Related U.S. Application Data division of application No. 13/773,340, filed on Feb. 21, 2013, now Pat. No. 9,339,256.

(60) Provisional application No. 61/601,482, filed on Feb. 21, 2012.

(51) Int. Cl.
*A61B 8/14* (2006.01)
*G01S 7/52* (2006.01)
*G01S 15/89* (2006.01)
*G03B 42/06* (2021.01)

(52) U.S. Cl.
CPC .......... *A61B 8/4477* (2013.01); *A61B 8/4488* (2013.01); *A61B 8/461* (2013.01); *A61B 8/5207* (2013.01); *A61B 8/5246* (2013.01); *G01S 7/52022* (2013.01); *G01S 7/52042* (2013.01); *G01S 15/8915* (2013.01); *G01S 15/8922* (2013.01); *G01S 15/8929* (2013.01); *G01S 15/8979* (2013.01); *G01S 15/8993* (2013.01); *G01S 15/8997* (2013.01); *G03B 42/06* (2013.01); *A61B 8/488* (2013.01); *G01S 15/8959* (2013.01)

(58) Field of Classification Search
CPC . A61B 8/8207; A61B 8/5246; G01S 7/52022; G01S 7/52042; G01S 15/8915; G01S 15/5922; G01S 15/8929; G01S 15/8979; G01S 15/8993; G01S 15/8997; G01S 15/8959

See application file for complete search history.

(56) References Cited

U.S. PATENT DOCUMENTS

| | | |
|---|---|---|
| 2010/0298712 A1 | 11/2010 | Pelissier et al. |
| 2012/0253194 A1* | 10/2012 | Tamura ............... G01S 7/52095 600/438 |
| 2013/0317331 A1 | 11/2013 | Bechtel et al. |

* cited by examiner

DETERMINING MATERIAL STIFFNESS USING MULTIPLE APERTURE ULTRASOUND

CROSS REFERENCE TO RELATED APPLICATIONS

This application is a continuation of U.S. application Ser. No. 15/155,908, filed May 16, 2016, now U.S. Pat. No. 10,675,000, which is a division of U.S. application Ser. No. 13/773,340, filed Feb. 21, 2013, now U.S. Pat. No. 9,339, 256, which application claims the benefit of U.S. Provisional Application No. 61/601,482, filed Feb. 21, 2012, all of which are incorporated by reference herein.

This application is also related to the following U.S. patent applications: Ser. No. 11/865,501, filed Oct. 1, 2007, now U.S. Pat. No. 8,007,439, and titled "Method And Apparatus To Produce Ultrasonic Images Using Multiple Apertures"; Ser. No. 12/760,375, filed Apr. 14, 2010, published as 2010/0262013 and titled "Universal Multiple Aperture Medical Ultrasound Probe"; Ser. No. 12/760,327, filed Apr. 14, 2010, now U.S. Pat. No. 8,473,239, and titled "Multiple Aperture Ultrasound Array Alignment Fixture"; Ser. No. 13/279,110, filed Oct. 21, 2011, now U.S. Pat. No. 9,282,945, and titled "Calibration of Ultrasound Probes"; Ser. No. 13/272,098, filed Oct. 12, 2011 and titled "Multiple Aperture Probe Internal Apparatus and Cable Assemblies"; Ser. No. 13/272,105, filed Oct. 12, 2011, now U.S. Pat. No. 9,247,926, and titled "Concave Ultrasound Transducers and 3D Arrays"; Ser. No. 13/029,907, filed Feb. 17, 2011, now U.S. Pat. No. 9,146,313, and titled "Point Source Transmission And Speed-Of-Sound Correction Using Multi-Aperture Ultrasound Imaging"; and Ser. No. 13/690,989, filed Nov. 30, 2012 and titled "Motion Detection Using Ping-Based and Multiple Aperture Doppler Ultrasound."

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure generally relates to imaging methods and devices for determining a material stiffness using a multiple aperture ultrasound probe to produce and track ultrasonic shear waves.

BACKGROUND

Changes in tissue stiffness have long been associated with disease. Traditionally, palpation is one of the primary methods of detecting and characterizing tissue pathologies. It is well known that a hard mass within an organ is often a sign of an abnormality. Several diagnostic imaging techniques have recently been developed to provide for non-invasive characterization of tissue stiffness.

One measure of tissue stiffness is a physical quantity called Young's modulus, which is typically expressed in units of Pascals, or more commonly kilo Pascals (kPa). If an external uniform compression (or stress, S) is applied to a solid tissue and this induces a deformation (or strain, e) of the tissue, Young's modulus is defined simply as the ratio between applied stress and the induced strain:

$E = S/e.$

Hard tissues have a higher Young's modulus than soft tissues. Being able to measure the Young's modulus of a tissue helps a physician in differentiating between benign and malignant tumors, detecting liver fibrosis and cirrhosis, detecting prostate cancer lesions, etc.

A collection of diagnostic and imaging modalities and processing techniques have been developed to allow clinicians to evaluate tissue stiffness using ultrasonography. These techniques are collectively referred to herein as Elastography. In addition to providing information about tissue stiffness, some elastography techniques may also be used to reveal other stiffness properties of tissue, such as axial strain, lateral strain, Poisson's Ratio, and other common strain and strain-related parameters. Any of these or other strain-related parameters may be displayed in shaded grayscale or color displays to provide visual representations of such strain-related parameters. Such information may be displayed in relation to two or three dimensional data.

Elastography techniques may be broadly divided into two categories, "quasi-static elastography" techniques and "dynamic elastography" techniques.

In quasi-static elastography, tissue strain is induced by mechanical compression of a tissue region of interest, such as by pressing against a tissue with a probe a hand or other device. In other cases, strain may be induced by compression caused by muscular action or the movement of adjacent organs. Images of the tissue region of interest are then obtained in two (or more) quasi-static states, for example, no compression and a given positive compression. Strain may be deduced from these two images by computing gradients of the relative local shifts or displacements in the images along the compression axis. Quasi-static elastography is analogous to a physician's palpation of tissue in which the physician determines stiffness by pressing the tissue and detecting the amount the tissue yields under this pressure.

In dynamic elastography, a low-frequency vibration is applied to the tissue and the speed of resulting tissue vibrations is detected. Because the speed of the resulting low-frequency wave is related to the stiffness of the tissue in which it travels, the stiffness of a tissue may be approximated from wave propagation speed.

Many existing dynamic elastography techniques use ultrasound Doppler imaging methods to detect the speed of the propagating vibrations. However, inherent limitations in standard Doppler imaging present substantial challenges when attempting to measure the desired propagation speed. This is at least partly because the waves of most interest tend to have a significant propagation component in a direction perpendicular to the direction of the initial low-frequency vibration.

As used herein, the term dynamic elastography may include a wide range of techniques, including Acoustic Radiation Force Impulse imaging (ARFI); Virtual Touch Tissue Imaging; Shearwave Dispersion Ultrasound Vibrometry (SDUV); Harmonic Motion Imaging (HMI); Supersonic Shear Imaging (SSI); Spatially Modulated Ultrasound Radiation Force (SMURF) imaging.

SUMMARY OF THE DISCLOSURE

Performing Elastography with a multiple aperture ultrasound imaging (MAUI) probe provides unique advantages over prior systems and methods. For example, in some embodiments, high resolution and high frame-rate imaging capabilities of a multiple aperture probe may be combined in order to detect a propagating shear wave as perturbations in image frames. In other embodiments, multiple aperture Doppler imaging techniques may be used to determine a speed of a propagating shear wave. In some embodiments, either or both of these techniques may further benefit from pixel-based imaging techniques and point-source transmission techniques.

In some embodiments, an ultrasound imaging system is provided, comprising a first ultrasound transducer array configured to transmit a wavefront that induces a propagating shear wave in a region of interest, a second ultrasound transducer array configured to transmit circular waveforms into the region of interest and receive echoes of the circular waveforms, and a signal processor configured to form a plurality of B-mode images of the region of interest from the circular waveforms at a frame rate sufficient to detect the propagating shear wave in the region of interest.

In some embodiments, the first ultrasound transducer array comprises an array of phased-array elements. In other embodiments, the first ultrasound transducer array comprises an annular array of piezoelectric rings, and the signal processor is further configured to focus the wavefront at various depths by adjusting phasing delays. In another embodiment, the first ultrasound transducer array comprises a switched ring transducer. In yet an additional embodiment, the first ultrasound transducer array comprises a single piezoelectric transducer.

In some embodiments, the frame rate can be at least 500 fps, at least 1,000 fps, at least 2,000 fps, or at least 4,000 fps.

In one embodiment, the signal processor is further configured to calculate a speed of the propagating shear wave by identifying a first position of the shear wave in a first frame of the plurality of B-mode images, identifying a second position of the shear wave in a second frame of the plurality of B-mode images, determining a distance traveled by the shear wave between the first frame and the second frame, determining a time elapsed between the first frame and the second frame, and dividing the distance traveled by the time elapsed.

In some embodiments, the first frame is the result of combining sub-images formed by echoes received by multiple elements of the second ultrasound transducer array.

In another embodiment, the signal processor is configured to identify the propagating shear wave as a point cloud moving through the region of interest.

In one embodiment, the signal processor is configured to define an image window identifying a section of the region of interest with a combination of zooming, panning, and depth selection.

In some embodiments, the system is configured to display a contemporaneous B-mode image of a selected image window.

A method of determining a stiffness of a tissue with ultrasound is provided, the method comprising the steps of forming a baseline image of a region of interest with an ultrasound imaging system, transmitting an ultrasonic pulse configured to induce a propagating shear wave in the region of interest, imaging the region of interest at a frame rate sufficient to detect the propagating shear wave to form a plurality of image frames of the region of interest, subtracting the baseline image from at least two of the formed image frames to obtain at least two difference frames, determining a position of the propagating shear wave in the at least two difference frames, and calculating a propagation speed of the propagating shear wave in the region of interest from the positions in the at least two difference frames.

In some embodiments, the method further comprises calculating a tissue stiffness of the region of interest from the propagation speed.

In one embodiment, the transmitting step comprises transmitting an ultrasonic pulse with a first ultrasound transducer array, and wherein the imaging step comprises imaging the region of interest with a second ultrasound transducer array.

In another embodiment, the forming step comprises transmitting a circular waveform from a first transmit aperture and receiving echoes on a first receive aperture.

In yet another embodiment, the imaging step comprises transmitting a circular waveform from the first transmit aperture and receiving echoes of the circular waveform with the first receive aperture.

In some embodiments, the first transmit aperture and the first receive aperture do not include overlapping transducer elements.

In another embodiment, the frame rate is at least 500 fps, at least 1,000 fps, at least 2,000 fps, or at least 4,000 fps.

In some embodiments, the method further comprises identifying the propagating shear wave as a point cloud moving through the region of interest.

In another embodiment, the method further comprises displaying a contemporaneous image of the region of interest, including a line indicating a direction of transmission of the ultrasonic pulse configured to induce a propagating shear wave.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
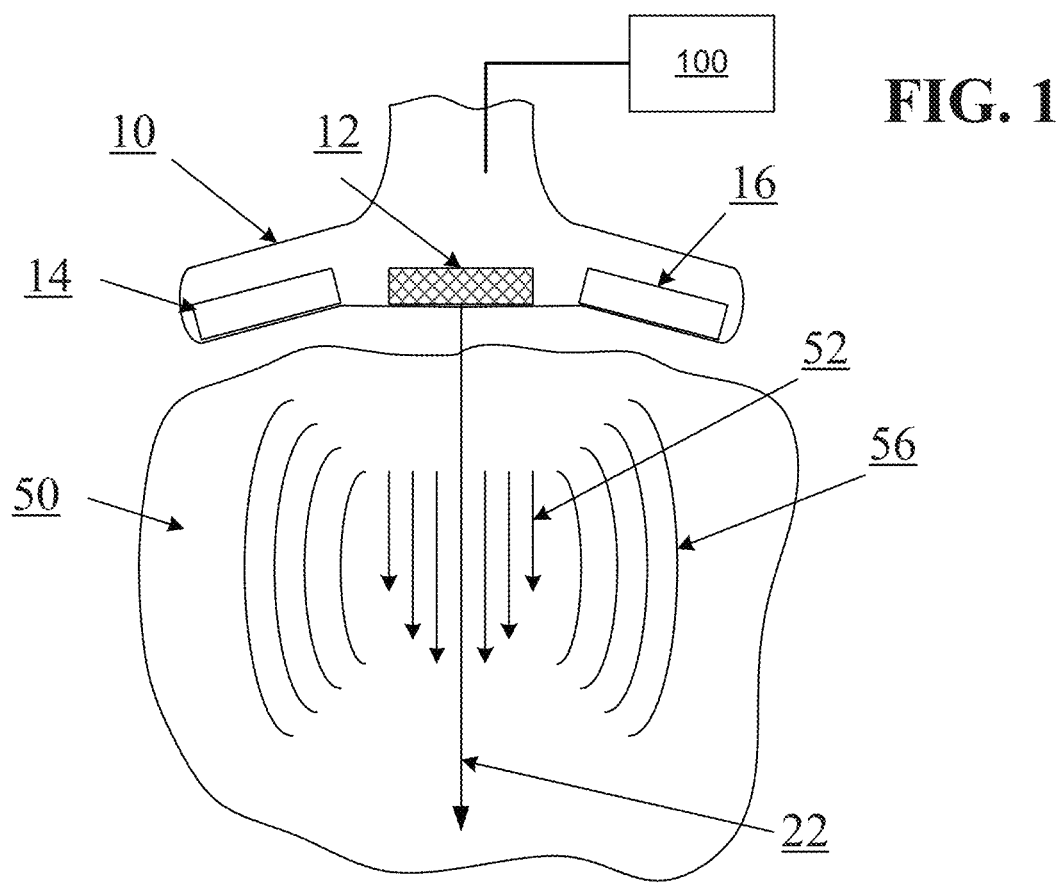
FIG. 1 is a schematic illustration of one embodiment of a multiple aperture ultrasound elastography probe and a propagating shear wave in a region of interest within a viscoelastic medium.

The various embodiments will be described in detail with reference to the accompanying drawings. References made to particular examples and implementations are for illustrative purposes, and are not intended to limit the scope of the invention or the claims.

In some embodiments, ultrasound imaging methods are provided in which a mechanical wave having a shear component and a compression component is generated in a viscoelastic medium (such as biological tissue). The speed of the resulting shear wave propagation may be measured while imaging the medium at a high frame-rate as the shear wave propagates through the medium. Speed of the propagating shear wave may be determined by identifying the changing position of the shear wave in a plurality of frames obtained at known time intervals. As will be described in further detail below, various embodiments of ping-based and multiple aperture ultrasound imaging are particularly well-suited to obtaining high resolution and high frame-rate images for performing accurate analysis of tissue stiffness using these methods. In some embodiments a qualitative and/or quantitative analysis of received echo data may be performed to identify regions of different hardness as compared with the rest of the viscoelastic medium.

Embodiments herein provide systems and methods for performing ultrasound elastography to determine the shear modulus of a tissue. In some embodiments, a method of determining a shear modulus comprises transmitting a mechanical shear wave into a test medium, then imaging the test medium using a high frame rate B-mode ultrasound imaging technique as the shear wave propagates through the medium. By comparing each image frame taken during propagation of the shear wave with a reference image generated prior to transmitting the shear wave, a propagation velocity may be determined.

Although the various embodiments are described herein with reference to imaging and evaluating stiffness of various anatomic structures, it will be understood that many of the methods and devices shown and described herein may also be used in other applications, such as imaging and evaluating non-anatomic structures and objects. For example, the ultrasound probes, systems and methods described herein may be adapted for use in non-destructive testing or evaluation of various mechanical objects, structural objects or materials, such as welds, pipes, beams, plates, pressure vessels, layered structures, soil, earth, concrete, etc. Therefore, references herein to medical or anatomic imaging targets, tissues, or organs are provided merely as non-limiting examples of the nearly infinite variety of targets that may be imaged or evaluated using the various apparatus and techniques described herein.

Introduction to Key Terms & Concepts

As used herein the terms "ultrasound transducer" and "transducer" may carry their ordinary meanings as understood by those skilled in the art of ultrasound imaging technologies, and may refer without limitation to any single component capable of converting an electrical signal into an ultrasonic signal and/or vice versa. For example, in some embodiments, an ultrasound transducer may comprise a piezoelectric device. In other embodiments, ultrasound transducers may comprise capacitive micromachined ultrasound transducers (CMUT).

Transducers are often configured in arrays of multiple individual transducer elements. As used herein, the terms "transducer array" or "array" generally refers to a collection of transducer elements mounted to a common backing plate. Such arrays may have one dimension (1D), two dimensions (2D), 1.X dimensions (e.g., 1.5D, 1.75D, etc.) or three dimensions (3D) (such arrays may be used for imaging in 2D, 3D or 4D imaging modes). Other dimensioned arrays as understood by those skilled in the art may also be used. Annular arrays, such as concentric circular arrays and elliptical arrays may also be used. An element of a transducer array may be the smallest discretely functional component of an array. For example, in the case of an array of piezoelectric transducer elements, each element may be a single piezoelectric crystal or a single machined section of a piezoelectric crystal.

As used herein, the terms "transmit element" and "receive element" may carry their ordinary meanings as understood by those skilled in the art of ultrasound imaging technologies. The term "transmit element" may refer without limitation to an ultrasound transducer element which at least momentarily performs a transmit function in which an electrical signal is converted into an ultrasound signal. Similarly, the term "receive element" may refer without limitation to an ultrasound transducer element which at least momentarily performs a receive function in which an ultrasound signal impinging on the element is converted into an electrical signal. Transmission of ultrasound into a medium may also be referred to herein as "insonifying." An object or structure which reflects ultrasound waves may be referred to as a "reflector" or a "scatterer."

As used herein, the term "aperture" may refer to a conceptual "opening" through which ultrasound signals may be sent and/or received. In actual practice, an aperture is simply a single transducer element or a group of transducer elements that are collectively managed as a common group by imaging control electronics. For example, in some embodiments an aperture may be a physical grouping of elements which may be physically separated from elements of an adjacent aperture. However, adjacent apertures need not necessarily be physically separated.

It should be noted that the terms "receive aperture," "insonifying aperture," and/or "transmit aperture" are used herein to mean an individual element, a group of elements within an array, or even entire arrays with in a common housing, that perform the desired transmit or receive function from a desired physical viewpoint or aperture. In some embodiments, such transmit and receive apertures may be created as physically separate components with dedicated functionality. In other embodiments, any number of send and/or receive apertures may be dynamically defined electronically as needed. In other embodiments, a multiple aperture ultrasound imaging system may use a combination of dedicated-function and dynamic-function apertures.

As used herein, the term "total aperture" refers to the total cumulative size of all imaging apertures. In other words, the term "total aperture" may refer to one or more dimensions defined by a maximum distance between the furthest-most transducer elements of any combination of send and/or receive elements used for a particular imaging cycle. Thus, the total aperture is made up of any number of sub-apertures designated as send or receive apertures for a particular cycle. In the case of a single-aperture imaging arrangement, the total aperture, sub-aperture, transmit aperture, and receive aperture will all have the same dimensions. In the case of a multiple aperture imaging arrangement, the dimensions of the total aperture includes the sum of the dimensions of all send and receive apertures.

In some embodiments, two apertures may be located adjacent one another on a continuous array. In still other embodiments, two apertures may overlap one another on a continuous array, such that at least one element functions as part of two separate apertures. The location, function, number of elements and physical size of an aperture may be defined dynamically in any manner needed for a particular application. Constraints on these parameters for a particular application will be discussed below and/or will be clear to the skilled artisan.

Elements and arrays described herein may also be multi-function. That is, the designation of transducer elements or arrays as transmitters in one instance does not preclude their immediate redesignation as receivers in the next instance. Moreover, embodiments of the control system herein include the capabilities for making such designations electronically based on user inputs, pre-set scan or resolution criteria, or other automatically determined criteria.

Inducing Shear Waves

The propagation velocity of shear waves in tissue is related to the stiffness (Young's modulus or shear modulus) and density of tissue by the following equation:

$$E = 3\rho \cdot c^2$$

where c is the propagation velocity of shear wave, E is Young's modulus, and $\rho$ is the tissue density. Because the density of tissues tends to vary minimally, and because the speed term is squared, elasticity may be calculated by assuming an approximate density value and measuring only the speed of shear wave propagation. In some cases, the assumed density value may vary depending on known information about the tissue being imaged, such as an approximate range of densities for known organ tissues. For example, liver tissue may have a density of approximately 1.05 kg/l, heart tissue may be about 1.03 kg/l, and skeletal muscle tissue may be about 1.04 kg/l. Variations in tissue elasticity are known to be associated with various disease states. Therefore, cancers or other pathological conditions may be detected in tissue by measuring the propagation velocity of shear waves passing through the tissue.

In some embodiments, a shear wave may be created within tissue by applying a strong ultrasound pulse to the tissue. In some embodiments, the shear wave generating ultrasound pulse (also referred to herein as an "initiating" pulse or an "init" pulse) may exhibit a high amplitude and a long duration (e.g., on the order of 100 microseconds). The ultrasound pulse may generate an acoustic radiation force to push the tissue, thereby causing layers of tissue to slide along the direction of the ultrasound pulse. These sliding (shear) movements of tissue may be considered shear waves, which are of low frequencies (e.g., from 10 to 500 Hz) and may propagate in a direction perpendicular to the direction of the ultrasound pulse.

Ultrasound shear waves typically result in only a few microns of tissue displacement. Since this amount is less than the resolution of most imaging systems, detecting the displacement carries additional challenges. In some embodiments, tissue displacement induced by shear waves may be detected in terms of the phase shift of the return of B-mode imaging echoes.

The propagation speed of a shear wave is typically on the order of about 1 to 10 m/s (corresponding to tissue elasticity from 1 to 300 kPa). Consequently, a propagating shear wave may cross a 6 cm wide ultrasound image plane in about 6 to 60 milliseconds. Thus, in order to collect at least three images of a fast-moving shear waves in a 6 cm wide image, a frame rate of at least 500 frames per second may be required. Most current radiology ultrasound systems refresh a complete image only every 17 to 33 milliseconds (corresponding to frame rates of about 58 to about 30 frames per second), which is too slow to image a propagating shear wave because the shear wave will have disappeared from the field of view before a single frame can be acquired. In order to capture shear waves in sufficient detail, frame rates of a thousand or more images per second are needed.

High Frame Rate Ultrasound Imaging

The frame rate of a scanline-based ultrasound imaging system is the pulse-repetition frequency (PRF, which is limited by the round-trip travel time of ultrasound in the imaged medium) divided by the number of scanlines per frame. Typical scanline-based ultrasound imaging systems use between about 64 and about 192 scanlines per frame, resulting in typical frame rates of only about 50 frames per second.

By using ping-based ultrasound imaging techniques, some ultrasound imaging systems and methods are capable of achieving frame rates on the order of thousands of frames per second. Some embodiments of such systems and methods are able to obtain an entire 2D image from a single transmit pulse, and can achieve a pulse rate (and therefore, a frame rate) of 4000 per second or higher when imaging to a depth of 18 cm. With this refresh rate it is possible to capture a shear wave at increments of about 2.5 mm of travel for the fastest waves, and even shorter increments for slower shear waves. When imaging at shallower depths, even higher frame rates may be achieved. For example, when imaging at a depth of 2 cm, a ping-based ultrasound imaging system may achieve a pulse rate (and therefore, a frame rate) of about 75,000 frames per second. Still higher frame rates may be achieved by transmitting overlapping pulses or pings (e.g., as described below).

In contrast to conventional scanline-based phased array ultrasound imaging systems, some embodiments of multiple aperture ultrasound imaging systems may use point source transmission during the transmit pulse. An ultrasound wavefront transmitted from a point source (also referred to herein as a "ping" or an unfocused ultrasound wavefront) illuminates the entire region of interest with each circular or spherical wavefront. Echoes received from a single ping received by a single receive transducer element may be beamformed to form a complete image of the insonified region of interest. Combining data and images from multiple receive transducers across a wide probe, and combining data from multiple pings, very high resolution images may be obtained. Moreover, such a system allows for imaging at a very high frame rate, since the frame rate is limited only by the ping repetition frequency—i.e., the inverse of the round-trip travel time of a transmitted wavefront traveling between a transmit transducer element, a maximum-depth reflector, and a furthest receive transducer element. In some embodiments, the frame rate of a ping-based imaging system may be equal to the ping repetition frequency alone. In other embodiments, if it is desired to form a frame from more than one ping, the frame rate of a ping-based imaging system may be equal to the ping repetition frequency divided by the number of pings per frame.

As used herein the terms "point source transmission" and "ping" may refer to an introduction of transmitted ultrasound energy into a medium from a single spatial location. This may be accomplished using a single ultrasound transducer element or combination of adjacent transducer elements transmitting together. A single transmission from said element(s) may approximate a uniform spherical wave front, or in the case of imaging a 2D slice it creates a uniform circular wave front within the 2D slice. In some cases, a single transmission of a circular or spherical wave front from a point source transmit aperture may be referred to herein as a "ping" or a "point source pulse" or an "unfocused pulse."

Point source transmission differs in its spatial characteristics from a scanline-based "phased array transmission" or a "directed pulse transmission" which focuses energy in a particular direction (along a scanline) from the transducer element array. Phased array transmission manipulates the phase of a group of transducer elements in sequence so as to strengthen or steer an insonifying wave to a specific region of interest.

In some embodiments, multiple aperture imaging using a series of transmit pings may operate by transmitting a point-source ping from a first transmit aperture and receiving echoes of the transmitted ping with elements of two or more receive apertures. A complete image may be formed by triangulating the position of reflectors based on delay times between transmission and receiving echoes. As a result, each receive aperture may form a complete image from echoes of each transmitted ping. In some embodiments, a single time domain frame may be formed by combining images formed from echoes received at two or more receive apertures from a single transmitted ping. In other embodiments, a single time domain frame may be formed by combining images formed from echoes received at one or more receive apertures from two or more transmitted pings. In some such embodiments, the multiple transmitted pings may originate from different transmit apertures.

"Beamforming" is generally understood to be a process by which imaging signals received at multiple discrete receptors are combined to form a complete coherent image. The process of ping-based beamforming is consistent with this understanding. Embodiments of ping-based beamforming generally involve determining the position of reflectors corresponding to portions of received echo data based on the path along which an ultrasound signal may have traveled, an assumed-constant speed of sound and the elapsed time between a transmit ping and the time at which an echo is received. In other words, ping-based imaging involves a calculation of distance based on an assumed speed and a measured time. Once such a distance has been calculated, it is possible to triangulate the possible positions of any given reflector. This distance calculation is made possible with accurate information about the relative positions of transmit and receive transducer elements and the speed-of-ultrasound in the imaged medium. As discussed in Applicant's previous applications referenced above, multiple aperture and other probes may be calibrated to determine the acoustic position of each transducer element to at least a desired degree of accuracy, and such element position information may be digitally stored in a location accessible to the imaging or beamforming system.

FIG. 1 schematically illustrates one embodiment of a multiple aperture ultrasound probe 10 configured for performing elastography. The probe 10 of FIG. 1 includes two imaging transducer arrays 14, 16 and one shear wave initiating transducer array, which is referred to herein as an "init" transmit transducer array 12. An init transducer array may be configured for transmitting a relatively low frequency shear-wave initiating pulse (also referred to herein as an "init pulse").

The probe 10 may also be configured to be connected to an electronic controller 100 configured to electronically control transmitted and received ultrasonic signals. The controller may be configured to transmit phased array or ping ultrasound signals, to receive and process echoes received by the imaging transducer arrays, to perform a receive beamforming process, and to form B-mode images from the received and processed echoes. The controller 100 may also be configured to control transmission of shear wavefronts from the init array, and may be configured determine a position of a shear wave and an elasticity of tissue in a region of interest according to any of the embodiments described herein. The controller 100 may also be configured to control image formation, image processing, echo data storage, or any other process, including the various methods and processes described herein. In some embodiments, some or all of the controller 100 can be incorporated into the probe. In other embodiments, the controller can be electronically coupled to the probe (e.g., by a wired or wireless electronic communication method), but physically separate from the probe itself. In still further embodiments, one or more separate additional controllers may be electronically connected to the probe 10 and/or to the controller 100. Such additional controllers may be configured to execute any one or more of the methods or processes described herein.

In the embodiment illustrated in FIG. 1, the init transducer array 12 is located centrally in between left 14 and right 16 lateral imaging transducer arrays. In alternative embodiments, an init array may be located in any other position, such as the left position 14, the right position 16 or another position in addition to those shown in FIG. 1. In further embodiments, any one of several transducer arrays in a multiple aperture probe may be temporarily or permanently assigned and controlled to operate as an init array.

In further embodiments, an init transducer need not necessarily be a separate array. Rather, a single transducer element or a group of transducer elements that are part of a larger array that may otherwise be used for imaging may be temporarily or permanently designated and controlled/operated as an init array.

As will be discussed in further detail below, the imaging transducer arrays 14, 16 of the probe 10 may be used for imaging the region of interest 50. The imaging transducer arrays 14, 16 may comprise any transducer array construction suitable for ultrasound imaging, such as 1D, 1.XD, 2D arrays of piezoelectric crystals or CMUT elements.

Figure 2:
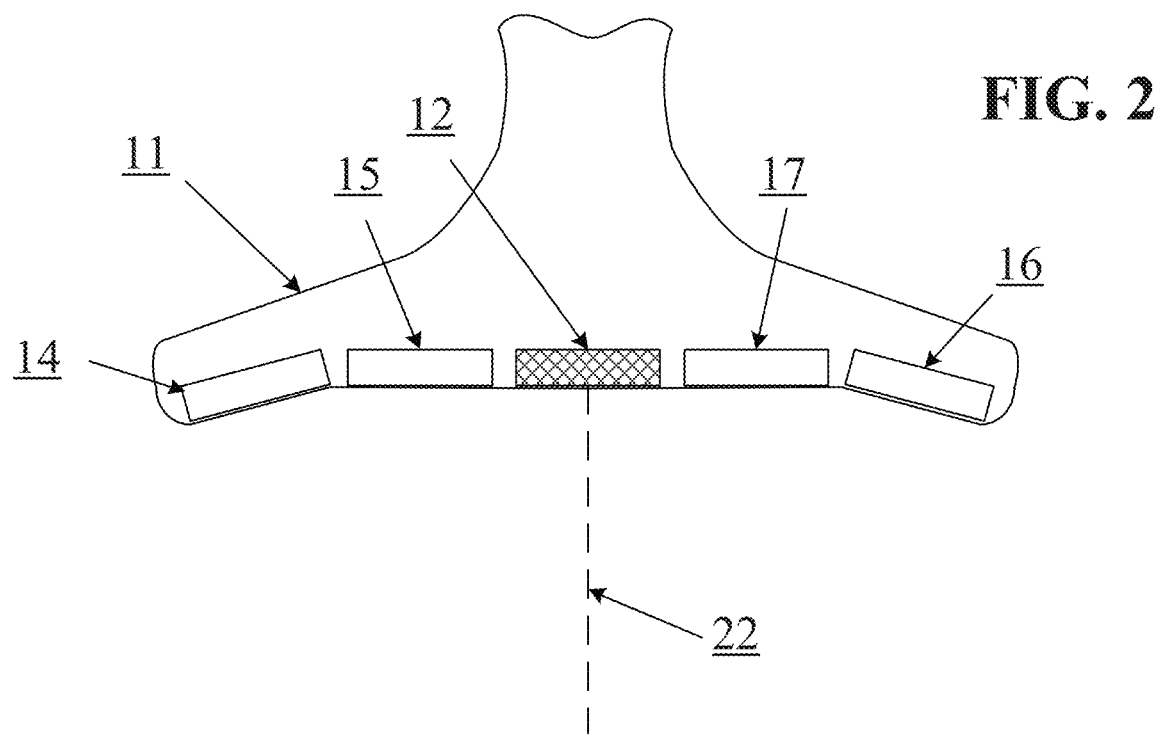
FIG. 2 is a schematic illustration of an embodiment of a multiple aperture ultrasound elastography probe having one shear wave initiating transducer array and four imaging transducer arrays.

Embodiments of multiple aperture ultrasound imaging probes may include any number of imaging apertures in a wide range of physical arrangements. For example, FIG. 2 illustrates an embodiment of a multiple aperture elastography probe 11 comprising a central init transducer array 12 and two pairs of imaging arrays 14, 15, 16, 17 all four of which may be used in a multiple aperture imaging process. In some embodiments, the init array 12 may alternatively be in the position of any of the other arrays 14, 15, 16, 17.

In some embodiments, multiple aperture probes may have a generally concave tissue-engaging surface, and may include a plurality of imaging apertures. In some embodiments, each individual aperture of a multiple aperture probe may comprise a separate and distinct transducer array. In other embodiments, individual apertures may be dynamically and/or electronically assigned on a large continuous transducer array.

Figure 3:
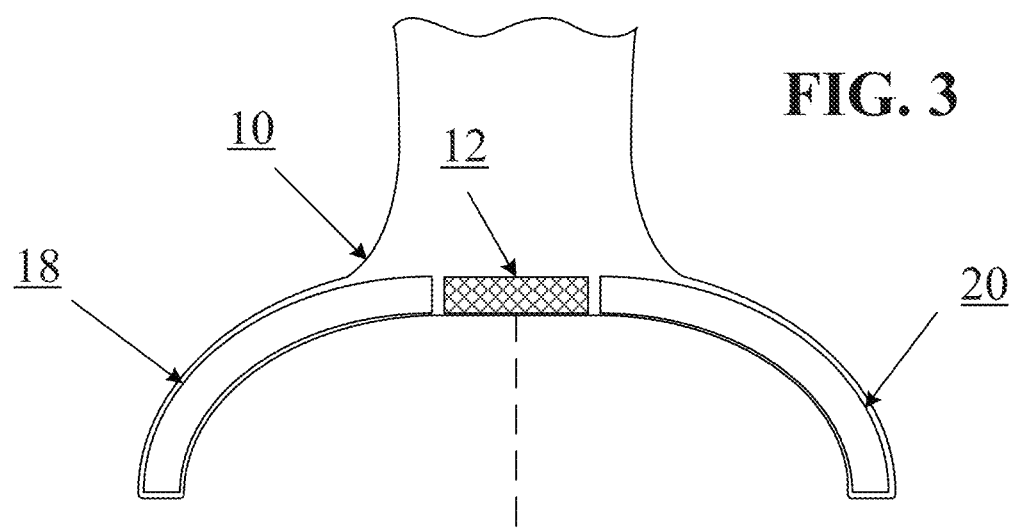
FIG. 3 is a schematic illustration of an embodiment of a multiple aperture ultrasound elastography probe having one shear wave initiating transducer array and two concave curved imaging transducer arrays.

FIG. 3 illustrates an embodiment of a multiple aperture elastography probe comprising a central init transducer array 12 and a pair of concave curved lateral imaging arrays 18, 20. In some embodiments, multiple imaging apertures may be dynamically assigned on one or both of the concave lateral arrays 18, 20 as described in Applicant's prior U.S. patent Application Ser. No. 13/272,105, now U.S. Pat. No. 9,247,926, which is incorporated herein by reference. Alternatively, each of the concave curved lateral arrays may be treated as a separate aperture.

Figure 3A:
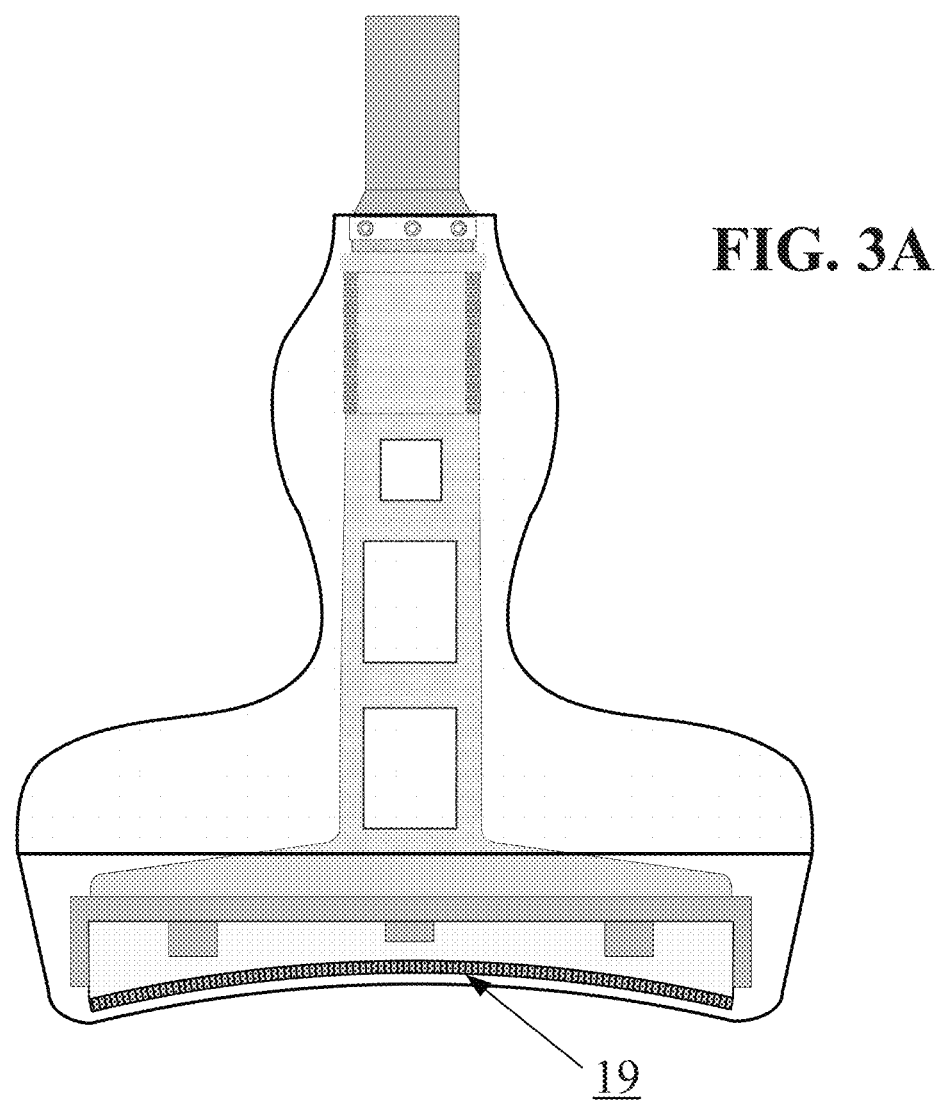
FIG. 3A is an illustration of an embodiment of a multiple aperture ultrasound elastography probe having a section of a continuous concave curved array designated as a shear-wave pulse initiating area.

FIG. 3A illustrates an embodiment of a multiple aperture elastography probe comprising a single continuous concave curved transducer array 19. As with other embodiments discussed above, any portion of the continuous curved array 19 may be temporarily or permanently configured, designated, and controlled/operated as an init array.

Figure 3B:
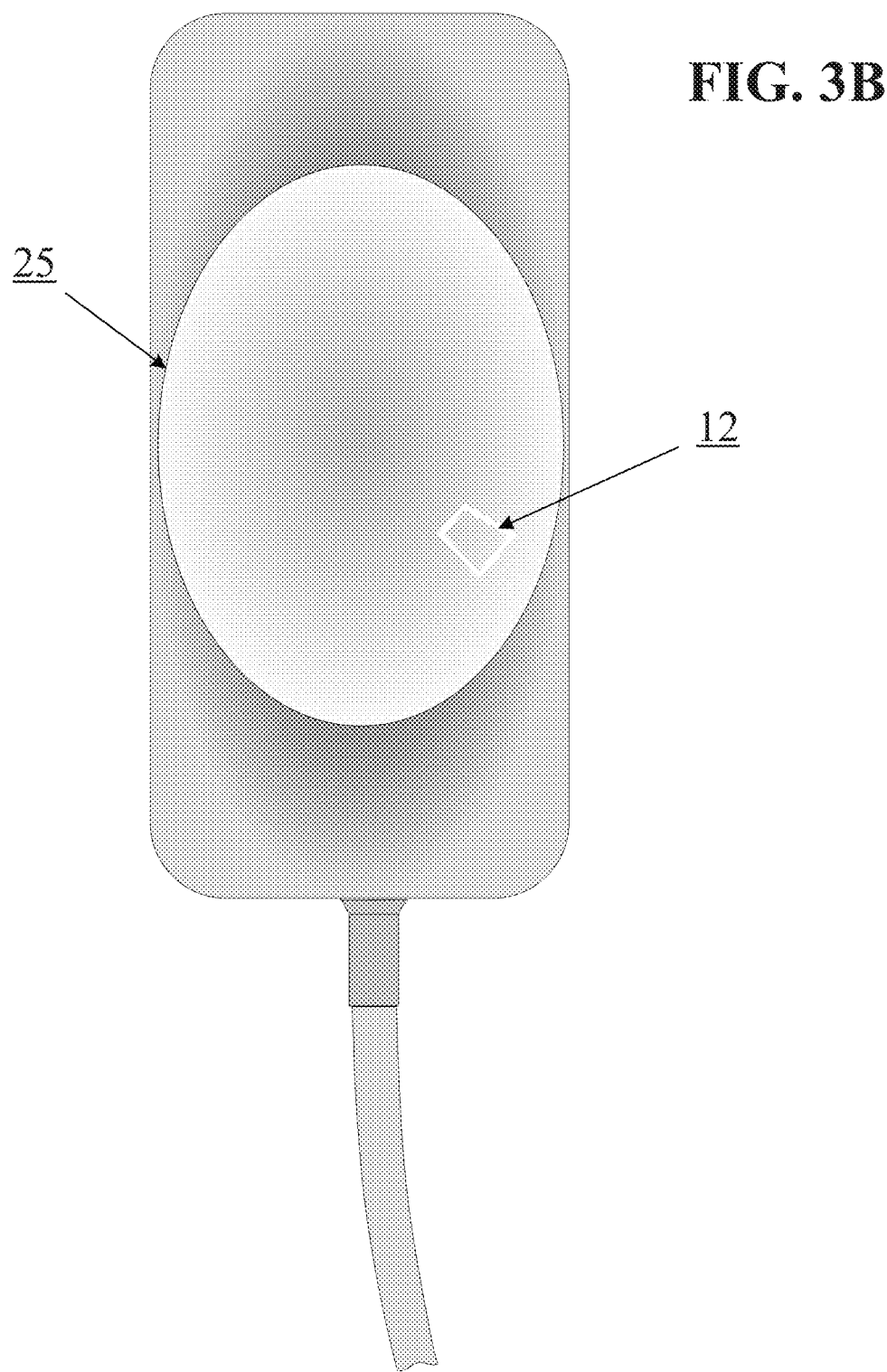
FIG. 3B is an illustration of an embodiment of a multiple aperture ultrasound elastography probe comprising a continuous 2D concave transducer array configured for 3D imaging with one group of elements designated as a shear-wave pulse initiating area.

FIG. 3B illustrates an embodiment of a multiple aperture elastography probe comprising a 3D array 25 as described in Applicant's prior application Ser. No. 13/272,105, now U.S. Pat. No. 9,247,926. A group of transducer elements 12 is shown designated as a shear wave initiating region. As with the above embodiments, any other region of the 3D array 25 may be designated as an init region.

In some embodiments, a probe with at least three arrays may be adapted for elastography by replacing at least one transducer array with a low frequency init transducer array. In some embodiments, an init transducer array of a multiple aperture probe may be positioned between at least two other arrays. Such probe configurations may include adjustable probes, cardiac probes, universal probes, intravenous ultrasound (IVUS) probes, endo-vaginal probes, endo-rectal probes, transesophageal probes or other probes configured for a particular application.

Similarly, any other multiple aperture or single-aperture ultrasound imaging probe may be adapted for use with the elastography systems and methods described herein. In still further embodiments, an init array may be provided on a separate probe entirely independent of an imaging probe. For example, an init probe may be provided with a separate housing from the housing of the imaging probe. In some embodiments, an independent init probe may be configured to be temporarily attached to an imaging probe. In such embodiments, such a separate init probe may be controlled by the same ultrasound imaging system as an imaging probe, or the init probe may be controlled independently of the imaging system. An independently-controlled elastography init pulse controller may be synchronized with an ultrasound imaging system in order to provide the imaging system with accurate timing information indicating the time at which an init pulse is transmitted.

In alternative embodiments, similar frame rates may be achieved by transmitting a plane wave front (e.g., by transmitting simultaneous pulses from several transducers in a common array), receiving echoes, and mapping the received echoes to pixel locations using techniques similar to those described above. Some embodiments of such plane-wave transmitting systems may achieve frame rates similar to those achieved with ping-based imaging techniques.

Embodiments of Shear-Wave Initiating Transducers

Regardless of probe construction, embodiments of an init array 12 may be configured to transmit shear-wave initiating ultrasound pulses with frequencies between about 1 MHz and about 10 MHz. In other embodiments, the init array 12 may be configured to transmit shear-wave initiating ultrasound pulses with a frequency up to about 18 MHz or higher. In some embodiments, an ultrasound frequency for producing init pulses may be about half of an ultrasound frequency used for imaging. Depending on materials and construction, a single transducer array may be capable of producing both low frequency ultrasound pulses for an init pulse and relatively high frequency ultrasound pulses for imaging. However, in some embodiments it may be desirable to use transducers optimized for a relatively narrow frequency range to allow for more efficient control of an init pulse or an imaging pulse.

Thus, in some embodiments, an init transducer array 12 may comprise a separate array configured to function exclusively as an init array, such as by being optimized to function efficiently within an expected init frequency range. As a result, in some embodiments an init array may be structurally different than separate imaging arrays. In other embodiments an init array may be physically identical to an imaging array, and may differ only in terms of its operation and use.

In some embodiments, the init transducer array 12 may comprise a rectangular or otherwise shaped array (e.g., a 1D, 1.xD, 2D or other rectangular array) of piezoelectric elements. In other embodiments, the init transducer array 12 may comprise a rectangular or otherwise shaped array of capacitive micro-machined ultrasound transducer (CMUT) elements.

Figure 4:
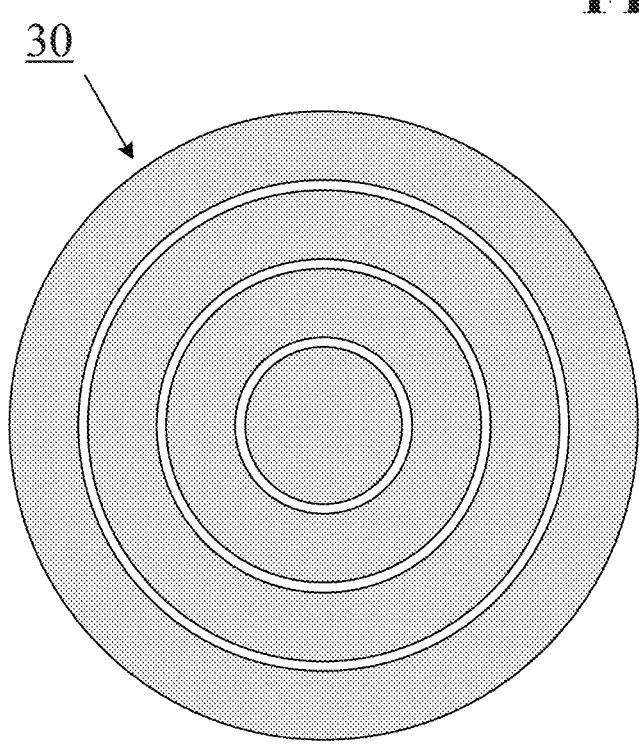
FIG. 4 is a schematic illustration of an annular array which may be used for the shear wave initiating transducer array or one or more of the imaging transducer arrays.

In other embodiments, the init array 12 may comprise an annular array 30 as shown for example in FIG. 4. An annular array may comprise a plurality of transducer elements arranged in concentric circular or elliptical patterns. Such annular arrays 20 may also use any suitable transducer material. In some embodiments, an init array 12 may comprise a switched ring annular transducer array.

In some embodiments, a switched-ring annular array may include a dish-shaped ultrasonic transducer (e.g., a segment of a sphere) which may be divided into a plurality of concentric annular transducer elements of which the innermost element may be either a planar annulus or a complete dish. In some embodiments, the curvature of the front surface of the annular array 20 and any lens or impedance matching layer between the transducer and the region of interest surface may at least partially determine the focal length of the transducer. In other embodiments, an annular array may be substantially planar and an acoustic lens may be employed to focus the transmitted ultrasound energy.

An annular array 20 may include any number of rings, such as three rings in addition to the center disc as shown in FIG. 4. In other embodiments, an annular array may include 2, 4, 5, 6, 7, 8, 9, 10 or more rings in addition to a center disc or dish. In some embodiments, the rings may be further decoupled by etching, scribing, complete cutting or otherwise dividing the rings into a plurality of ring elements within each ring. In some embodiments, an annular array transducer for operating to depths of 25 cm may have a diameter of 40 mm with the outer ring may have a width of approximately 1.85 mm, providing a surface area of 222 $mm^2$; the inner ring may have a width of approximately 0.8 mm and lying at an approximate radius of 10.6 mm to provide a surface area of 55 $mm^2$.

In some embodiments, each ring (or each ring element within a ring) may have individual electrical connections such that each ring (or ring element) may be individually controlled as a separate transducer element by the control system such that the rings may be phased so as to direct a shear-wave initiating pulse to a desired depth within the region of interest. The amplitude of the energy applied may determine the amplitude of the emitted ultrasonic waves which travel away from the face of the annular array 20.

In some embodiments the size and/or number of elements in an init array may be determined by the shape or other properties of the shear waves to be produced.

In some embodiments, a shear-wave initiating pulse produced by an init transducer array 12 may be focused during transmission to provide maximum power at the region of interest. In some embodiments, the init pulse may be focused on an init line 22 (e.g., as shown in FIGS. 1, 2 and 3). The init pulse may further be focused at a desired depth to produce a maximum disruptive power at the desired depth. In some embodiments, the axial focus line and the focused depth point may be determined by transmitting pulses from a plurality of transducer elements at a set of suitable delays (i.e., using "phased array" techniques). In some embodiments, transmit delays may be omitted when using an annular array with a series of switched rings as discussed above.

In some embodiments, the init pulse need not be electronically steerable. In such embodiments, the probe may be configured to always transmit an init pulse along a consistent line relative to the probe. In some embodiments, the expected line of the init pulse may be displayed on the ultrasound display (e.g., overlaying a contemporaneous B-mode image of the region of interest) so as to provide an operator with a visual indication of the path of the init pulse relative to the imaged region of interest. In such embodiments, a sonographer may manipulate the probe until the display shows a representative init line passing through an object to be evaluated by elastography.

In alternative embodiments, an init pulse may be electronically steered in a direction indicated by an operator. In such embodiments, the line of the init pulse may be selected by an operator through any appropriate user interface interaction without the need to move the probe. In some embodiments, the user interface interaction may include a visual display of the init line on a display screen (e.g., overlaying a contemporaneous B-mode image of the region of interest). Once a desired init pulse direction is chosen, an init pulse may be electronically steered so as to travel along the selected line.

Embodiments for Detecting Shear Wave Propagation Rate

Returning to FIG. 1, an example of shear wave propagation will be described. A shear wave may be initiated in a region of interest 50 from an init pulse from a multiple aperture elastography probe 10 (or any other suitably configured elastography probe). As discussed above, the init pulse may be focused along a line 22 extending from the init transducer array 12 into the region of interest to at least a desired depth. In some embodiments, the line 22 may be perpendicular to the init transducer array 12. An initial pulse 52 transmitted along the init line 22 will tend to induce a wave front 56 propagating outwards from the line 22 within the image plane. The propagating wavefront 56 induced by the init pulse will push the tissue in the direction of propagation. An elastic medium such as human tissue will react to this push by a restoring force which induces mechanical waves including shear waves which propagate transversely from the line 22 in the tissue.

Embodiments of elastographic imaging processes will now be described with reference to the probe construction of FIG. 1 and the flow charts of FIGS. 5-7. These processes may be used with any suitably configured probe as described above. In some embodiments, the left and right lateral transducer arrays 14, 16 may be used to image the region of interest 50 with either, both or a combination of a high frame rate ultrasound imaging technique and a high resolution multiple aperture ultrasound imaging technique. These techniques are summarized below, and further details of these techniques are provided in U.S. patent application Ser. No. 13/029,907, now U.S. Pat. No. 9,146,313, which illustrates embodiments of imaging techniques using transmission of a circular wavefront and using receive-only beamforming to produce an entire image from each pulse or "ping" (also referred to as ping-based imaging techniques).

The terms "high resolution imaging" and "high frame rate imaging" are used herein as abbreviated names for alternative imaging processes. These terms are not intended to be limiting or exclusive, as the "high resolution imaging" process may also be operated at a high frame rate relative to other imaging techniques, and the "high frame rate imaging" process may also produce images of a substantially higher resolution than other imaging techniques. Furthermore, the rate of shear wave propagation may be detected using high frame rate imaging techniques and/or high resolution imaging techniques other than those described or referenced herein.

Figure 5:
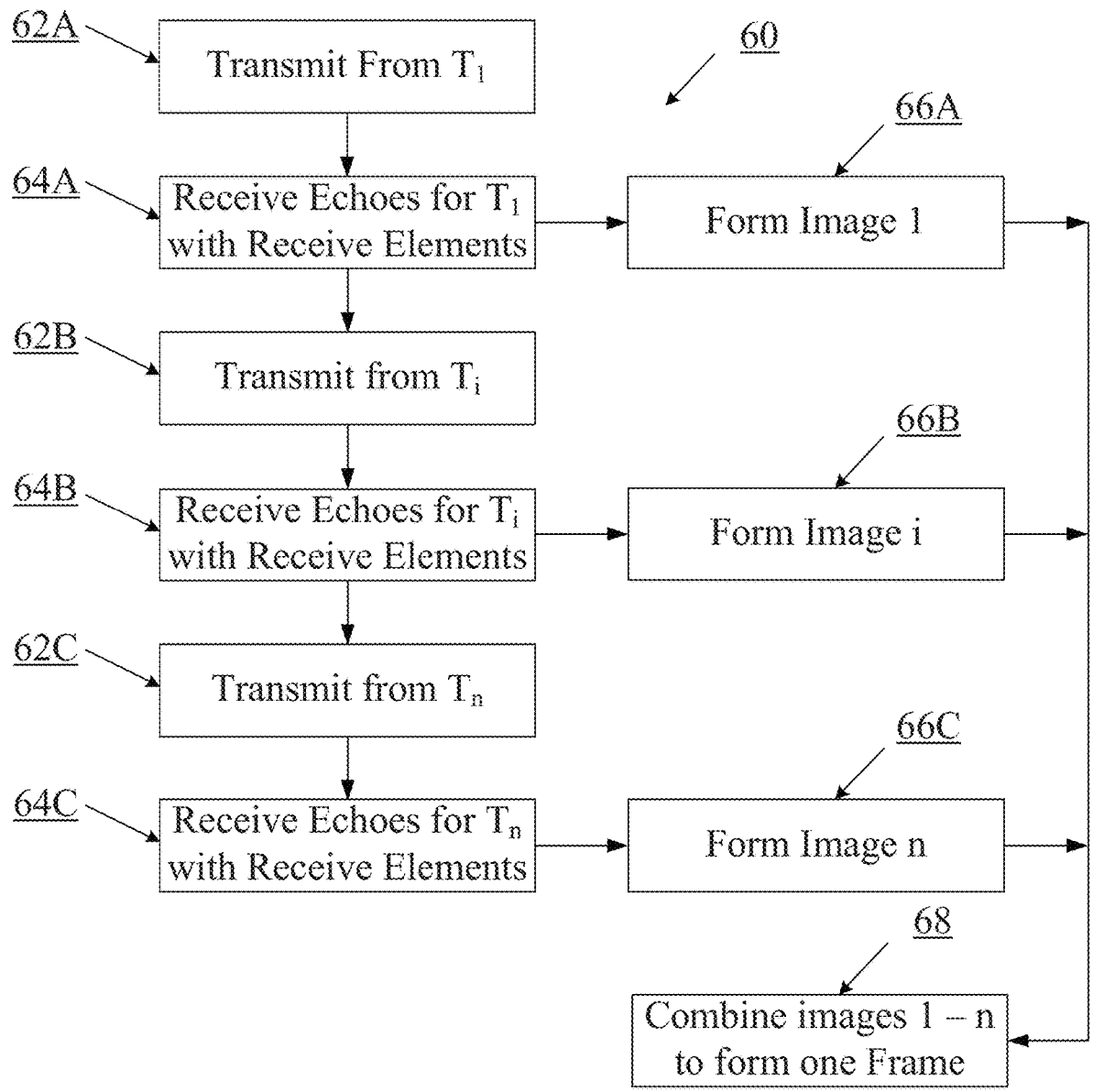
FIG. 5 is a flow chart illustrating one embodiment of a high resolution multiple aperture imaging process.

FIG. 5 illustrates an embodiment of a high resolution multiple aperture imaging process 60 that may use a multiple aperture ultrasound imaging probe such as that shown in FIG. 1. In some embodiments, one or both of the imaging arrays 14, 16 may include one or more transducer elements temporarily or permanently designated as transmit elements T1 through Tn. The remaining transducer elements of one or both of the imaging arrays 14, 16 may be designated as receive elements.

In some embodiments, a high resolution multiple aperture ultrasound imaging process 60 may comprise transmitting a series of successive pulses from a series of different transmit apertures (T1 . . . Tn) 62, receiving echoes 64 from each pulse with a plurality of elements on a receive aperture, and obtaining a complete image 66 from echoes received from each transmit pulse. These images may then be combined 68 into a final high-resolution image. Embodiments of such a high resolution multiple aperture imaging process may be substantially similar to the process shown and described in Applicant's prior U.S. patent application Ser. No. 13/029,907, now U.S. Pat. No. 9,146,313, referenced above.

As indicated in FIG. 5, during a first cycle of a high resolution imaging process, the steps of transmitting an ultrasound signal 62A, receiving echoes 64A, and forming an image 66A may be performed using a first transmit transducer T1. During a second cycle, signals may be transmitted 62B from a different transmit transducer T1, echoes may be received 64B, and a second image may be formed 66B. The process of steps 62x-66x may be repeated using n different transmit transducers which may respectively be located at any desired position within an ultrasound probe. Once a desired number of image (also referred to as image layers) have been formed, such image layers may be combined 68 into a single image frame, thereby improving image quality. If desired, the process 60 may then be repeated to obtain multiple time-domain frames which may then be consecutively displayed to a user.

Figure 6:
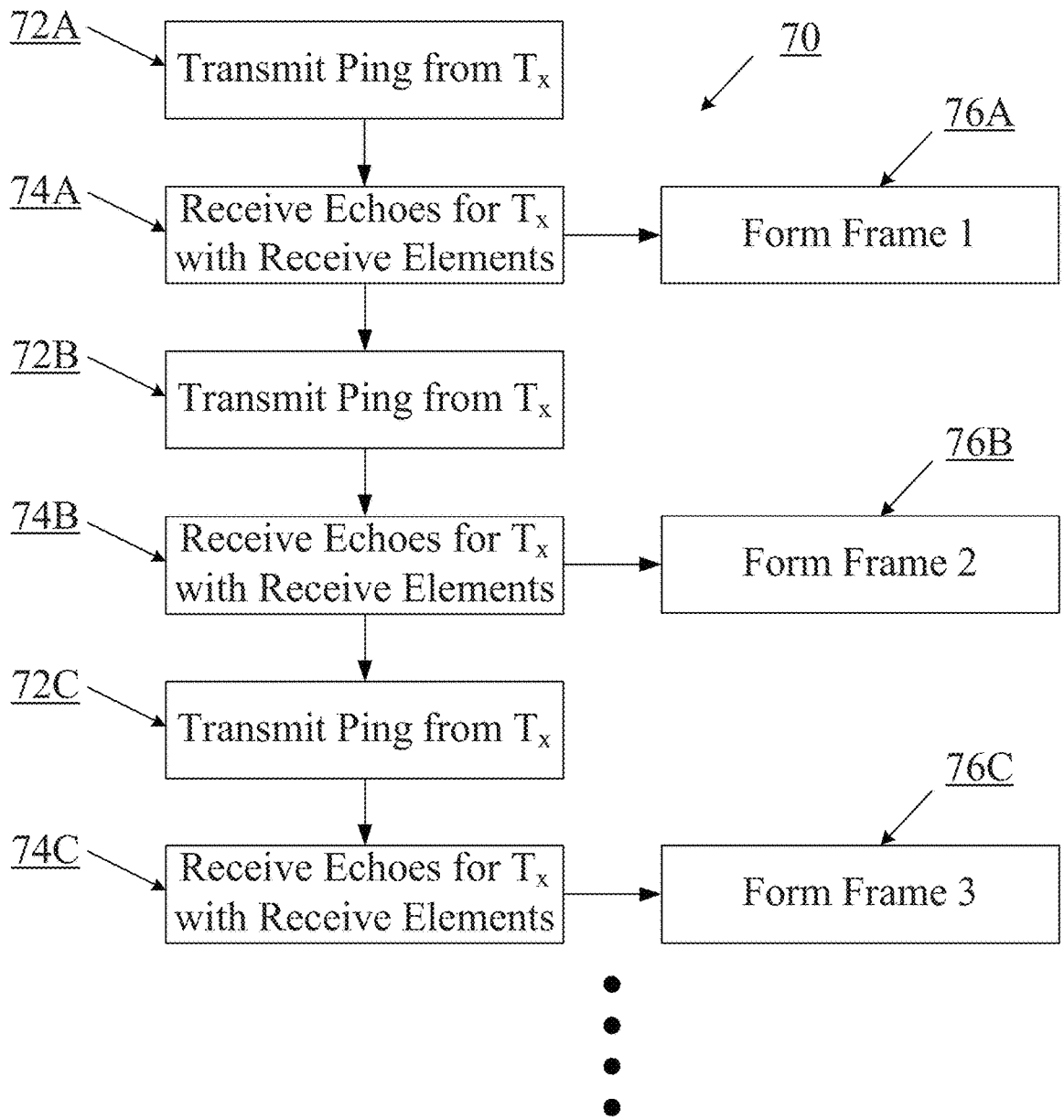
FIG. 6 is a flow chart illustrating one embodiment of a high frame rate multiple aperture imaging process.

FIG. 6 illustrates an embodiment of a high frame rate imaging process 70. In some embodiments, a high frame rate ultrasound imaging process 70 may comprise transmitting successive pings from a single transmit aperture Tx 72, forming a complete image 76 from echoes received 74 from each transmitted ping 72, and treating each image 76 as a successive time domain frame. In this way, slight changes in the position of reflectors in the region of interest 50 can be sampled at a very high frame rate.

As indicated in FIG. 6, during a first cycle, a ping may be transmitted from a chosen transmit transducer Tx 72A, echoes may be received 74A and a first frame may be formed 76A. The same cycle of steps transmitting 72B and receiving 74B may then be repeated to produce a second frame 76B, a third frame (steps 72C, 74C, 76C), and as many subsequent frames as desired or needed as described elsewhere herein.

In some embodiments, a maximum frame rate of an imaging system using ping-based imaging techniques may be reached when a ping repetition frequency (i.e., the frequency at which successive pings are transmitted) is equal to an inverse of the round trip travel time (i.e., the time for an ultrasound wave to travel from a transmit transducer to a reflector at a desired distance from the transducer, plus the time for an echo to return from the reflector to a receive transducer along the same or a different path). In other embodiments, overlapping pings may be used with coded excitation or other methods of distinguishing overlapping echoes. That is, a second ping may be transmitted before all echoes from a first ping are received. This is possible as long as the transmitted ping signals may be coded or otherwise distinguished such that echoes of a first ping may be recognized as distinct from echoes of a second ping. Several coded excitation techniques are known to those skilled in the art, any of which may be used with a point-source multiple aperture imaging probe. Alternatively, overlapping pings may also be distinguished by transmitting pings at different frequencies or using any other suitable techniques. Using overlapping pings, even higher imaging frame rates may be achieved.

In some embodiments, prior to initiating an elastographic imaging process, an imaging window may be defined during a B-mode imaging process. The defined image window may be a section of the region of interest in which elastography is to be performed. For example, the image window may be defined after any combination of probe positioning, depth-selection, zooming, panning, etc. In some embodiments, an image window may be as large as an entire insonified region of interest. In other embodiments, an image window may be only a smaller section of the complete region of interest (e.g., a "zoomed-in" section). In some embodiments, an image window may be defined after an imaging session using echo data retrieved from a raw data memory device.

Figure 7:
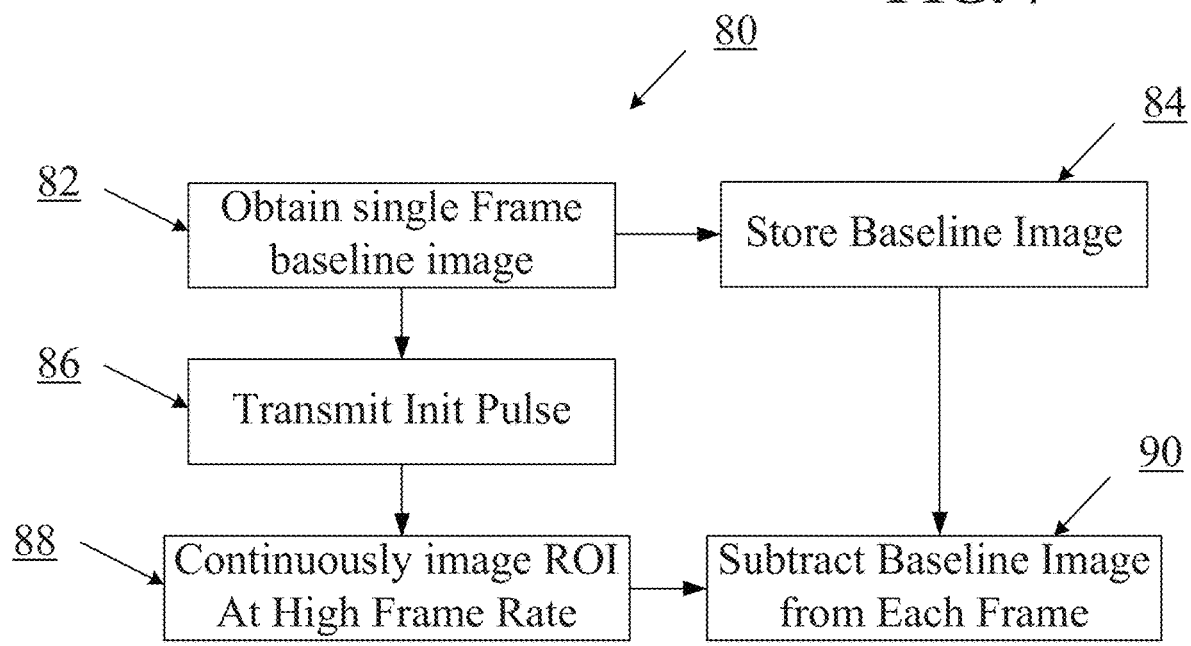
FIG. 7 is a flow chart illustrating one embodiment of an elastography data capture process.

FIG. 7 illustrates an embodiment of an elastography process 80 using a probe such as that shown in FIG. 1. In the illustrated embodiment, an elastography process 80 may generally involve the steps of obtaining 82 and storing 84 a baseline image, transmitting a shear-wave initiating pulse (an init pulse) 86 into the region of interest 50, imaging the region of interest 50 using a high frame rate imaging process 88, and subtracting the baseline image 90 from each frame obtained during the high frame rate imaging process 88. The remaining series of "difference frames" can then be analyzed to obtain information about the tissue displaced by the shear wave 56 propagating through the tissue of the region of interest 50. The propagation speed of the shear wave 56 may be obtained through analysis of the perturbation of tissue in the time-series of difference frames.

In some embodiments, while imaging a selected image window within a region of interest with an elastography-enabled ultrasound probe, an init line 22 (shown in FIG. 1) may be displayed on an ultrasound image display screen overlying an image of the target region. In some embodiments, the ultrasound imaging system may continuously image the region of interest with a high resolution imaging process as discussed above with reference to FIG. 5. Alternatively, any other desired ultrasound imaging process may be used to obtain an image of the region to be analyzed by an elastography process.

Once the probe 10 is in a desired orientation such that the init line 22 intersects a desired target object or portion of the region of interest, an elastography depth may be selected, and an elastography process 80 may be initiated. In some embodiments, an elastography depth may be selected by an operator via a suitable user interface action. In other embodiments, an elastography depth may be selected automatically by an ultrasound imaging control system. In some embodiments, an elastography process may be initiated manually by an operator of the ultrasound system. In other embodiments, an elastography process 80 may be initiated automatically by an ultrasound system upon automatic identification of a structure to be inspected.

As shown in the embodiment of FIG. 7, an elastography process 80 using a probe such as that shown in FIG. 1 (or any other suitably configured probe) may begin by obtaining 82 and storing 84 a baseline image of the target region of interest 50. In one embodiment, the baseline image may be formed by obtaining a single frame using a high-frame-rate imaging process such as that described above. In such embodiments, a baseline image may be formed by transmitting an imaging pulse from a single transducer element Tx from a first of the lateral transducer arrays 14, 16 (e.g., the right array 16), and receiving echoes on multiple elements of the second of the lateral transducer arrays 14, 16 (e.g., the left array 14). In some embodiments, echoes from the transmit pulse may also be received by receive elements on the first transducer array (e.g., the right array 16). The baseline image may then be formed and stored 84 for use in subsequent steps. In an alternative embodiment, the baseline image may be obtained 82 using a high resolution imaging process such as that described above.

After obtaining a baseline image 82, the init transducer array may be operated to transmit a shear-wave initiating pulse 86 into the region of interest. An init pulse may be produced by any suitable devices and methods as described above. In some embodiments, the shear wave initiating pulse may be focused along a displayed init line 22, and may be focused at a particular depth within the region of interest.

After an init pulse is transmitted 86, the system may begin imaging the region of interest at a high frame rate 88 using the lateral imaging arrays 14, 16. In some embodiments, the high frame rate imaging process may comprise the process described above with reference to FIG. 6. In one embodiment, the high frame rate imaging process may comprise transmitting a series of transmit pulses from a single transmit aperture Tx, and receiving echoes at a plurality of elements on at least one receive aperture. In some embodiments, the high frame rate imaging 88 may be performed by transmitting ultrasound pulses from the same transmit element (or aperture) as that used in the step of obtaining a baseline image 82. In some embodiments, the high frame rate imaging may continue at least until propagation of the induced shear wave has stopped or has progressed to a desired degree. A duration of high frame-rate imaging time may be calculated in advance based on an expected minimum propagation speed and an image size. Alternatively, the high frame rate imaging 88 may be stopped upon detecting the shear wave's propagation at an extent of an imaging frame.

In some embodiments, forming a single frame during a high frame rate imaging process 88 may include combining image layers obtained from echoes received at different receiving transducer elements. For example, separate images may be formed from echoes received by each individual transducer element of a receive aperture to form a single improved image. Then, a first image produced by echoes received by all elements of a first receive aperture may be combined with a second image produced by echoes received by all elements of a second receive aperture in order to further improve the quality of the resulting image. In some embodiments, the image resulting from such combinations may then be used as a single frame in the high frame rate imaging process 88. Further examples of such image combining are described in U.S. patent application Ser. No. 13/029,907, now U.S. Pat. No. 9,146,313, referenced above.

In some embodiments, the baseline image may then be subtracted 90 from each individual frame obtained in the high frame rate imaging process 88. For example, each pixel value of a single frame may be subtracted from the value of each corresponding pixel in the baseline image. The image resulting from such subtraction may be referred to as a "difference image" or a "difference frame." The difference images thus obtained will include pixel values representing substantially only the shear waveform plus any noise.

In some embodiments, the steps of obtaining a baseline image 82, transmitting an init pulse 86 continuously imaging at a high frame rate 88, and obtaining difference image frames 90 may be repeated as many times as desired. The difference images from such multiple cycles may be averaged or otherwise combined in order to improve a signal to noise level.

The propagating shear waveform may be detected along lines transverse to the direction of the init pulse (e.g., as shown in FIG. 1) by detecting perturbation (i.e., small changes in an otherwise 'normal' pattern) in subsequent difference frames. The speed of the shear wave's propagation may be obtained by determining the position of the shear wave in multiple image frames obtained at known time intervals.

Figure 8:
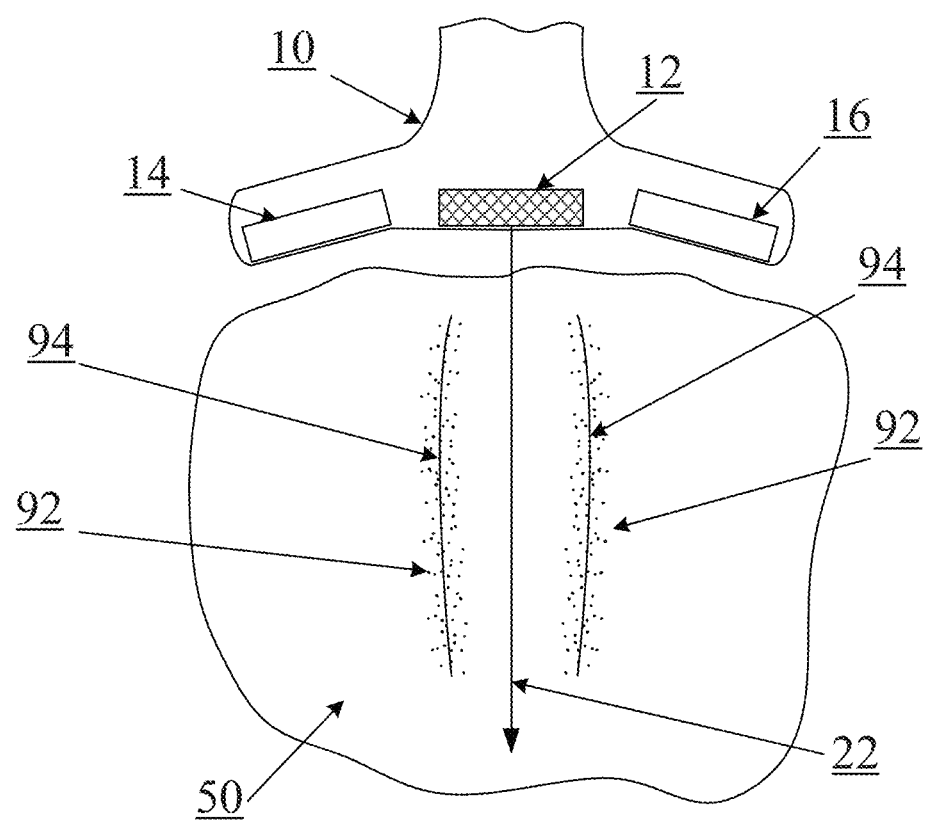
FIG. 8 is an example of a difference frame showing perturbation caused by a propagating shear wave.

In some cases, the perturbation caused by a propagating shear wave may produce a relatively disbursed image of the propagating wave front. For example, perturbation may appear in a difference frame as a speckle pattern 92 such as that shown in FIG. 8. An approximate center line 94 of the point cloud 92 may be determined and treated as representative of the position of the propagating shear wavefront. In some embodiments, a line, curve or other path 94 may be fit to the point cloud 92 using any suitable path fit algorithm. For example, in some embodiments an absolute value of the difference frame may be calculated, and a local position of the shear wave may be determined by averaging the position of the nearest x points.

In some embodiments, the analysis may be limited to only a portion of the point cloud 92 (and/or a corresponding center line 94). For example, if it is determined (by visual inspection or by automated analysis) that a small segment of the shear wavefront is propagating faster than adjacent segments, the region(s) of apparent higher or lower propagation speed may be selected, and the speed of propagation may be calculated for only that portion of the shear wavefront.

By calculating a distance between the focused init line 22 and the fit line 94 in a given difference frame, an approximate position of the shear wave in the given difference frame may be calculated. The rate of propagation of the wavefront between any two frames may be determined by dividing the distance traveled by the shear wave by the time that elapsed between obtaining the two frames. In alternative embodiments, the position of a shear wave in any given frame may be measured relative to any other suitable datum.

In various embodiments, the number of frames needed to measure the propagation speed of a shear wave may vary. In some embodiments an approximate speed measurement may be obtained from as few as two or three frames obtained at known time intervals. In other embodiments, at least ten frames obtained at known time intervals may be needed to obtain a sufficiently accurate time measurement. In further embodiments, at least 100 frames obtained at known time intervals may be used to obtain a more accurate time measurement. In still further embodiments, 200 frames or more may be used. Generally, the accuracy of shear wave propagation speed measurements may increase with the number of frames from which such measurements are made. As the number of frames increases, so does computational complexity, so the number of frames to be used may be balanced with available processing capabilities.

When more than two frames are available to be used for measuring propagation speed, any number of algorithms may be used. For example, in some embodiments the shear wave position may be detected in each available frame, a speed may be calculated between each consecutive pair of frames, and the results of all such speed measurements may be averaged to obtain a single speed value. In other embodiments, speed measurements may be calculated based on time intervals and relative shear wave positions between different and/or variable numbers of frames. For example, propagation speed may be calculated between every three frames, every five frames, every 10 frames, every 50 frames, etc. Such measurements may then be averaged with one another and/or with measurements obtained from consecutive frame pairs. Weighted averages may also be used in some embodiments.

In some embodiments, an entire elastography process 80 (FIG. 7) may be repeated at different focus depths relative to the init transducer array 12. In some embodiments, un-beamformed elastography echo data obtained at various depths may be stored and combined into a single 2D or 3D data set for further post processing and/or for later viewing and analysis. In various embodiments, un-beamformed elastography echo data may be captured and stored for later processing on the imaging system or any other suitable computing hardware.

In alternative embodiments, the propagation speed of a shear wave may be measured by detecting the speed of moving/displaced tissues using the multiple aperture Doppler techniques described in Applicant's U.S. patent application Ser. No. 13/690,989, filed Nov. 30, 2012, (now U.S. Pat. No. 10,226,234) titled "Motion Detection Using Ping-Based And Multiple Aperture Doppler Ultrasound."

Once the shear wave is captured and its propagation speed is measured, the hardness of the tissue in the region of interest, as quantified by Young's modulus (E) can be measured or determined by a controller, signal processor or computer. Elasticity (E) and shear wave propagation speed (c) are directly related through the simple formula:

$$E = 3\rho c^2$$

Where $\rho$ is the density of tissue expressed in kg/m$^3$. Because the density of tissues tends to vary minimally, an approximate density value may be assumed for the purpose of calculating elasticity using a measured propagation speed value. The fact that the speed term is squared further minimizes the effect of any error in the assumed density value. Thus, the elasticity of the tissue may be calculated after measuring only the shear wave propagation velocity c and using an assumed approximate value for tissue density.

In some embodiments, the density value may be stored in a digital memory device within or electronically accessible by the controller. In other embodiments, the density value may be manually entered or edited by a user via any suitable user interface device. Once the speed of shear wave propagation has been measured for a desired area within the region of interest, the controller may retrieve the density value and calculate the elasticity for the desired area.

In some embodiments, elasticity estimates may be overlaid on an image of the region of interest. In some embodiments, such an overlay may be provided as a color coded shaded image, showing areas of high elasticity in contrasting colors to areas of relatively low elasticity. Alternatively, a propagating shear wave may be displayed on an image. In some embodiments, a propagating shear wave may be displayed as an animated moving line, as changing colors, as a moving point cloud or in other ways. In further embodiments, a numeric value of a shear wave propagation speed may be displayed. In other embodiments, numeric values of elasticity may be displayed on an image of the region of interest. Soft tissues will tend to have relatively small values of elasticity, and liquid-filled areas do not conduct shear waves at all.

Raw Echo Data Memory

Various embodiments of the systems and methods described above may be further enhanced by using an ultrasound imaging system configured to store digitized echo waveforms during an imaging session. Such digital echo data may be subsequently processed on an imaging system or on an independent computer or other workstation configured to beamform and process the echo data to form images. In some embodiments, such a workstation device may comprise any digital processing system with software for dynamically beamforming and processing echo data using any of the techniques described above. For example, such processing may be performed using data processing hardware that is entirely independent of an ultrasound imaging system used to transmit and receive ultrasound signals. Such alternative processing hardware may comprise a desktop computer, a tablet computer, a laptop computer, a smartphone, a server or any other general purpose data processing hardware.

In various embodiments, received echo data (including echoes received during a high frame rate imaging process) may be stored at various stages from pure analog echo signals to fully processed digital images or even digital video. For example, a purely raw analog signal may be stored using an analog recording medium such as analog magnetic tape. At a slightly higher level of processing, digital data may be stored immediately after passing the analog signal through an analog-to-digital converter. Further processing, such as band-pass filtering, interpolation, downsampling, up-sampling, other filtering, etc. may be performed on the digitized echo data, and raw data may be stored after such additional filtering or processing steps. Such raw data may then be beamformed to determine a pixel location for each received echo, thereby forming an image. Individual images may be combined as frames to form video. In some embodiments, it may be desirable to store digitized echo data after performing very little processing (e.g., after some filtering and conditioning of digital echo data, but before performing any beamforming or image processing). Some ultrasound systems store beamformed echo data or fully processed image data. Nonetheless, as used herein, the phrases "raw echo data" and "raw data" may refer to stored echo information describing received ultrasound echoes (RX data) at any level of processing prior to beamforming. Raw echo data may include echo data resulting from B-mode pings, Doppler pings, or any other ultrasound transmit signal.

In addition to received echo data, it may also be desirable to store information about one or more ultrasound transmit signals that generated a particular set of echo data. For example, when imaging with a multiple aperture ping ultrasound method as described above, it is desirable to know information about a transmitted ping that produced a particular set of echoes. Such information may include the identity and/or position of one or more a transmit elements as well as a frequency, magnitude, pulse length, duration or other information describing a transmitted ultrasound signal. Transmit data is collectively referred herein to as "TX data".

In some embodiments, TX data may also include information defining a line along which a shear-wave initiating pulse is transmitted, and timing information indicating a time at which such a shear-wave initiating pulse is transmitted relative to received echo data.

In some embodiments, such TX data may be stored explicitly in the same raw data memory device in which raw echo data is stored. For example, TX data describing a transmitted signal may be stored as a header before or as a footer after a set of raw echo data generated by the transmitted signal.

In other embodiments, TX data may be stored explicitly in a separate memory device that is also accessible to a system performing a beamforming process. In embodiments in which transmit data is stored explicitly, the phrases "raw echo data" or "raw data" may also include such explicitly stored TX data. In still further embodiments, transducer element position information may be explicitly stored in the same or a separate memory device. Such element position data may be referred to as "calibration data" or "element position data", and in some embodiments may be generally included within "raw data."

TX data may also be stored implicitly. For example, if an imaging system is configured to transmit consistently defined ultrasound signals (e.g., consistent magnitude, shape, frequency, duration, etc.) in a consistent or known sequence, then such information may be assumed during a beamforming process. In such cases, the only information that needs to be associated with the echo data is the position (or identity) of the transmit transducer(s). In some embodiments, such information may be implicitly obtained based on the organization of raw echo data in a raw data memory. For example, a system may be configured to store a fixed number of echo records following each ping. In such embodiments, echoes from a first ping may be stored at memory positions 0 through 'n' (where 'n' is the number of records stored for each ping), and echoes from a second ping may be stored at memory positions n+1 through 2n+1. In other embodiments, one or more empty records may be left in between echo sets. In some embodiments received echo data may be stored using various memory interleaving techniques to imply a relationship between a transmitted ping and a received echo data point (or a group of echoes). Similarly, assuming data is sampled at a consistent, known sampling rate, the time at which each echo data point was received may be inferred from the position of that data point in memory. In some embodiments, the same techniques may also be used to implicitly store data from multiple receive channels in a single raw data memory device.

In some embodiments, raw TX data and raw echo data may be captured and stored during an imaging session in which an elastography process is performed. Such data may then be later retrieved from the memory device, and beamforming, image processing, and shear-wave speed measurement steps may be repeated using different assumptions, inputs or algorithms in order to further improve results. For example, during such re-processing of stored data, assumed values of tissue density or speed-of-sound may be used.

Beamforming, image layer combining, or speed measurement averaging algorithms may also be modified during such re-processing relative to a real-time imaging session. In some embodiments, while reprocessing stored data, assumed constants and algorithms may be modified iteratively in order to identify an optimum set of parameters for a particular set of echo data.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Various modifications to the above embodiments will be readily apparent to those skilled in the art, and the generic principles defined herein may be applied to other embodiments without departing from the spirit or scope of the invention. Thus, it is intended that the scope of the present invention herein disclosed should not be limited by the particular disclosed embodiments described above, but should be determined only by a fair reading of the claims that follow.

In particular, materials and manufacturing techniques may be employed as within the level of those with skill in the relevant art. Furthermore, reference to a singular item, includes the possibility that there are plural of the same items present. More specifically, as used herein and in the appended claims, the singular forms "a," "and," "said," and "the" include plural referents unless the context clearly dictates otherwise. As used herein, unless explicitly stated otherwise, the term "or" is inclusive of all presented alternatives, and means essentially the same as the commonly used phrase "and/or." Thus, for example the phrase "A or B may be blue" may mean any of the following: A alone is blue, B alone is blue, both A and B are blue, and A, B and C are blue. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

What is claimed is:

1. A method of determining a stiffness of a tissue with ultrasound, the method comprising the steps of:
   forming a baseline image of a region of interest with a ping-based ultrasound imaging system;
   transmitting an ultrasonic pulse with a shear-wave-initiating transducer, the ultrasonic pulse being configured to induce a propagating shear wave in the region of interest;
   imaging the region of interest with the ping-based ultrasound imaging system to capture a first image frame that includes a first speckle pattern caused by the propagating shear wave as it moves through the region of interest;
   imaging the region of interest with the ping-based ultrasound imaging system to capture a second image frame that includes a second speckle pattern caused by the propagating shear wave as it moves through the region of interest;
   subtracting the baseline image from the first image frame with an electronic controller of the ping-based ultrasound imaging system to obtain a first difference frame;
   subtracting the baseline image from the second image frame with the electronic controller to obtain a second difference frame;
   calculating a first distance between an init line of the ping-based ultrasound imaging system and the first speckle pattern of the first difference frame to determine a first position of the propagating shear wave;
   calculating a second distance between the init line of the ping-based ultrasound imaging system and the second speckle pattern of the second difference frame to determine a second position of the propagating shear wave; and
   calculating a propagation speed of the propagating shear wave in the region of interest from the first and second positions in the first and second difference frames.

2. The method of claim 1, further comprising determining a first center line of the first speckle pattern, wherein calculating the first distance further comprises calculating the first distance between the init line and the first center line to determine the first position of the propagating shear wave.

3. The method of claim 2, further comprising determining a second center line of the second speckle pattern, wherein calculating the second distance further comprises calculating the second distance between the init line and the second center line to determine the second position of the propagating shear wave.

4. The method of claim 1, wherein calculating the propagation speed further comprises dividing a distance traveled by the propagating shear wave between the first difference frame and the second difference frame by an elapsed time between the first difference frame and the second difference frame.

5. The method of claim 1, further comprising calculating a tissue stiffness of the region of interest from the propagation speed.

6. The method of claim 1, wherein transmitting the ultrasonic pulse comprises transmitting the ultrasonic pulse with a first ultrasound transducer array, and wherein imaging the region of interest comprises imaging the region of interest with a second ultrasound transducer array.

7. The method of claim 1, wherein transmitting the ultrasonic pulse comprises transmitting a first circular waveform from a first transmit aperture and receiving echoes on a first receive aperture.

8. The method of claim 1, wherein the frame rate is between 1,000 and 75,000 fps.

9. The method of claim 1, wherein the first difference frame and the second difference frame each contain substantially only noise and the first and second speckle patterns representing the propagating shear wave.

10. The method of claim 1, further comprising determining that a first segment of the shear wave is propagating faster than adjacent segments of the shear wave, and calculating a first segment propagation speed of the first segment.

* * * * *